United States Patent [19]

Yokoyama

[11] 4,312,870
[45] Jan. 26, 1982

[54] PYRAZOLOQUINOLINES

[75] Inventor: Naokata Yokoyama, Cliffside Park, N.J.

[73] Assignee: Ciba-Geigy Corporation, Ardsley, N.Y.

[21] Appl. No.: 150,398

[22] Filed: May 16, 1980

Related U.S. Application Data

[63] Continuation-in-part of Ser. No. 50,716, Jun. 21, 1979, abandoned.

[51] Int. Cl.³ .................... A61K 31/47; C07D 471/04
[52] U.S. Cl. ...................... 424/258; 546/82; 546/162
[58] Field of Search ............ 546/82; 424/258

[56] References Cited

U.S. PATENT DOCUMENTS

| | | | |
|---|---|---|---|
| 3,890,324 | 6/1975 | Katner | 424/232 |
| 4,076,818 | 2/1978 | Vogt | 424/251 |
| 4,112,096 | 9/1978 | Vogt | 424/251 |
| 4,112,098 | 9/1978 | Vogt | 424/251 |
| 4,146,621 | 3/1979 | Voorhees | 424/240 |
| 4,164,578 | 8/1979 | Vogt | 544/115 |
| 4,179,561 | 12/1979 | Vogt | 544/250 |
| 4,268,516 | 3/1980 | Lombardino et al. | 424/273 P |

OTHER PUBLICATIONS

Seka et al., Monatsh, 1931, vol. 57, pp. 52–62.
Hinton et al., J. Chem. Soc., 1959, pp. 599–610.

*Primary Examiner*—Henry R. Jiles
*Assistant Examiner*—Natalia Harkaway
*Attorney, Agent, or Firm*—Norbert Gruenfeld; Prabodh I. Almaula

[57] ABSTRACT

2-Aryl-pyrazolo[4-3-c]quinolin-3-ones, e.g. those of the formula

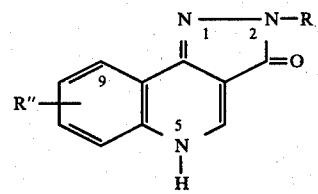

R = phenyl, R"-phenyl, pyridyl, alkylpyridyl or halopyridyl;
R" = H, alkyl, alkoxy, alkylthio, OH, halo, $CF_3$, nitro, amino, mono- or dialkylamino, CN, carbamoyl or carboxy and pharmaceutically acceptable acyl derivatives or salts thereof, are psychoactive agents useful in the treatment of anxiety or depression.

16 Claims, No Drawings

PYRAZOLOQUINOLINES

CROSS-REFERENCE TO RELATED APPLICATION

This is a continuation-in-part of application Ser. No. 050,716, filed June 21, 1979 (now abandoned).

BACKGROUND OF THE INVENTION

2-Aryl-pyrazolo[4,3-c]quinolin-3-ones have not been described in the chemical literature yet. However, 2-unsubstituted 4-phenyl-pyrazolo[4,3-c]quinolin-3-ones, or 3-hydroxy-tautomers thereof respectively, are described in Monatsh. 57, 52 (1931). In contrast, 2-phenyl-pyrazolo[4,3-c]isoquinolin-3-ones (or 3-ols) are described in J. Chem. Soc. 1959, 599; and European Patent Application No. 5,745 discloses antiinflammatory, CNS-depressant and anti-anxiety 3-phenyl-pyrazolo[3,4-c]isoquinolin-5-ones.

SUMMARY OF THE INVENTION

The present invention concerns and has for its object the provision of new 2-aryl-pyrazolo[4,3-c]quinolin-3-(1 and 5H)-ones, more particularly of those corresponding to Formulae I and II

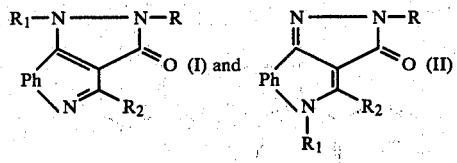

wherein Ph is 1,2-phenylene, unsubstituted or substituted by up to 3 identical or different members selected from lower alkyl, lower alkoxy, lower alkylthio, hydroxy, halogeno, trifluoromethyl, nitro, amino, mono- or di-lower alkylamino, cyano, carbamoyl and carboxy; R is unsubstituted or substituted phenyl as defined by H—Ph, pyridyl, lower alkylpyridyl, or halogenopyridyl; $R_1$ is hydrogen, lower alkyl or lower (hydroxy, dialkylamino or H—Ph)-alkyl; and $R_2$ is hydrogen or lower alkyl; their 3-hydroxy-tautomers; lower alkanoyl, carbamoyl, mono- or di-lower alkylcarbamoyl derivatives of said (hydroxy or amino)-(phenyl or phenylene) compounds; or pharmaceutically acceptable salts thereof; as well as of corresponding pharmaceutical compositions and of methods for the preparation and application of said products, which are useful psychoactive agents for the treatment of anxiety or depression in mammals.

DESCRIPTION OF THE PREFERRED EMBODIMENTS

The 1,2-phenylene group Ph is preferably unsubstituted, or but mono- or di-substituted, and its up to three substituents are illustrated by the following groups: lower alkyl, e.g. methyl, ethyl, n- or i-propyl or -butyl; lower alkoxy, e.g. methoxy, ethoxy, n- or i-propoxy or -butoxy; lower alkylthio, e.g. methylthio or ethylthio; hydroxy; halogeno, e.g. fluoro, chloro or bromo; trifluoromethyl; nitro; amino; mono- or di-lower alkylamino, e.g. mono- or di-(methyl, ethyl, n-or i-propyl)-amino; cyano, carbamoyl or carboxy.

The phenyl or pyridyl radical R in 2-position is preferably said ortho-unsubstituted phenyl group H—Ph, as defined for the unsubstituted or up to trisubstituted 1,2-phenylene Ph above, but also 3-,4- or preferably 2-pyridyl, or said alkylated or halogenated pyridyls, advantageously (4-methyl or 5-chloro)-2-pyridyl. Of said Ph- and/or R-substituents, listed above and starting from trifluoromethyl, preferably but one thereof is present.

The radical $R_1$, in either the 1- or preferably 5-position, is advantageously hydrogen, but also one of said alkyl groups, or a lower (hydroxy, dialkylamino or H—Ph)-alkyl group, which preferably separates adjacent hetero-atoms by at least 2 carbon atoms, such as 2-(hydroxy, dimethylamino or diethylamino)-ethyl, 2- or 3-(hydroxy or dimethylamino)-propyl; benzyl, 1- or 2-phenethyl.

The radical $R_2$ in 4-position is preferably also hydrogen, or one of said alkyl groups, advantageously methyl.

On account of said 1- or 5-substituents $R_1$, the compounds of this invention are correctly depicted as 3-ones, or 3-oxo-derivatives respectively. But in case $R_1=H$, they may also form a minor amount of 3-hydroxytautomers, depending on milieu and substitution. In general, they are but weak bases or acids respectively, forming acyl-derivatives only with said (hydroxy or amino)-Ph compounds, and salts with either strong acids or bases. Said acyl derivatives are the lower alkanoyl, carbamoyl, mono- or di-lower alkylcarbamoyl derivatives of the above (hydroxy or amino)-(phenyl or phenylene) compounds, e.g. the acetyl, propionyl, pivaloyl; (methyl or ethyl)-carbamoyl derivatives; and the salts are preferably alkali metal, e.g. sodium or potassium salts of the 1- or 5-unsubstituted compounds ($R_1=H$) and/or the carboxy-(phenyl or phenylene) compounds; or addition salts of all of said compounds with the pharmaceutically acceptable acids listed below.

The term "lower", referred to above or hereinafter in connection with organic radicals or compounds respectively, defines such with up to 7, preferably up to 4, and advantageously those with one or two carbon atoms.

The compounds of the invention exhibit valuable pharmacological properties, primarily antidepressant or anxiolytic effects. They are demonstrable by in vitro and in vivo tests, using advantageously mammals, e.g. mice, rats, or monkeys, as test objects. Said compounds can be applied to them enterally or parenterally, advantgeously orally, or subcutaneously, intravenously or intraperitoneally, for example, within gelatin capsules or in the form of starchy suspensions or aqueous solutions or suspensions respectively. The applied dosage may range between about 0.01 and 100 mg/kg/day, preferably between about 0.05 and 5 mg/kg/day, advantageously between about 0.1 and 0.5 mg/kg/day.

Said antidepressant properties can be shown in mice according to the Behavioral Despair test (Arch. Int. Pharmacodyn. Ther. 229 (2): 327–336, Oct. 1977). It induces a depressed state therein by forcing them to swim in a narrow cylinder from which they cannot escape. After a brief period of vigorous activity the mice adopt a characteristic immobile posture, which is readily identifiable. Immobility is reduced by the compounds of this invention, other tricyclic antidepressants, monoamine oxidase inhibitors, atypical antidepressants and electroconvulsive shock.

Anxiolytic effects are routinely observed, for example, according to the classical metrazole antagonism test in rats, or according to the Cook-Davidson conflict procedure, using male Wistar rats which are maintained at 80% of normal body weight by dietary-, but not water-restriction. They are trained to press a lever within a conditioning chamber, also containing a liquid dipper, a house light, a speaker and a grid-floor. Both lever and grid are connected to an electrical shock source and the chamber is situated in a sound-attenuated room in which a white noise-source is activated during testing, in order to mask any extraneous auditory cues. Each session of 47 minutes duration consists of two alternating schedules. The first is a Variable Interval (VI) schedule of 30 seconds, lasting for 5 minutes, during which a sweetened, condensed milk reinforcement is delivered following the first lever-press after the 30 seconds have elapsed, and a drug-induced decrement of this performance is taken as an indication of a neurological deficit. Immediately following the VI-schedule both a 1000 Hz tone and a light-cue are activated, indicating the commencement of the second, Fixed Ratio (FR) schedule, lasting for 2 minutes, wherein the milk reinforcement is delivered concomitant with an electric foot shock immediately following the tenth response, thereby establishing a conflict situation. The intensity of said shock ranges between 2.0 and 3.6 mA, varying with each animal, in order to adjust them to about 25–100 responses during this schedule over the entire session. A drug-induced enhancement of performance during the RF-schedule is taken as indication of antianxiety effects, as exhibited by said compounds of this invention.

The anxiolytic effects of said new compounds can also be estimated by the Diazepam Receptor Binding Assay in vitro, e.g. as described in Nature 266, 732 (1977) or Proc. Nat. Acad. Sci. USA 74, 3805 (1977). Diazepam binds specifically and with high affinity to crude synaptosomal membrane preparations from rat fore-brain. This binding is inhibited by other anxiolytic compounds, e.g. other pharmacologically more active benzo-diazepines. When tritiated diazepam is used, the interaction of other drugs with said receptor can be readily assessed thus: Membranes from rat fore-brain are incubated at 0°–5° with tritiated diazepam and various concentrations of the test substances in a physiological medium at the pH=7.5. The membranes, containing the receptors with various amounts of tritiated diazepam, are filtered onto glass fiber filters, which are then shaken in a liquid scintillation counter. The concentration of the compounds of this invention, required to inhibit the specific binding of 2 nM of tritiated diazepam by 50%, i.e. the $IC_{50}$, is determined graphically and ranges down to about 0.6 nM, what is an order of magnitude lower than the value for diazepam (5 nM) and almost four orders lower than the value for chlordiazepoxide (400 nM).

Accordingly, the compounds of this invention are useful in the treatment of mental depression and preferably for combatting anxiety problems similar to those treated with diazepam. In contrast to diazepam, said compounds of the invention appear to be devoid of neurological deficit liability at doses where anti-anxiety effects are already established. Finally, the compounds of the invention are also valuable intermediates in the preparation of other useful products, especially of corresponding pharmaceutical compositions.

Particularly useful are compounds of Formulae I and II wherein Ph is 1,2-phenylene, unsubstituted or substituted by one or two members selected from lower alkyl, lower alkoxy, lower alkylthio, hydroxy, halogeno, trifluoromethyl, nitro, amino, mono- or di-lower alkylamino, cyano, carbamoyl and carboxy; R is H—Ph, pyridyl, lower alkylpyridyl or halogenopyridyl; $R_1$ is hydrogen, lower alkyl or lower (hydroxy, dialkylamino or HPh)-alkyl, wherein the hydroxy or amino group is separated from the ring-nitrogen atom by at least 2 carbon atoms; and $R_2$ is hydrogen or lower alkyl; or lower alkanoyl, carbamoyl, mono- or di-lower alkylcarbamoyl derivatives of said (hydroxy or amino)-(phenyl or phenylene) compounds; or pharmaceutically acceptable alkali metal or acid addition salts thereof.

More preferred are those compounds of Formulae I and II, wherein Ph is 1,2-phenylene, (lower alkyl)-1,2-phenylene, (lower alkoxy)-1,2-phenylene, (lower alkylthio)-1,2-phenylene, (hydroxy)-1,2-phenylene, (halogeno)-1,2-phenylene, (trifluoromethyl)-1,2-phenylene, (nitro)-1,2-phenylene, (amino)-1,2-phenylene, (mono- or di-lower alkylamino)-1,2-phenylene, (cyano)-1,2-phenylene, (carbamoyl)-1,2-phenylene or (carboxy)-1,2-phenylene; R is H—Ph pyridyl, (lower alkyl)-pyridyl or (halogeno)-pyridyl; and each of $R_1$ and $R_2$ is hydrogen or lower alkyl; or lower alkanoyl, carbamoyl, mono- or di-lower alkylcarbamoyl derivatives of said (hydroxy or amino)-phenyl or phenylene) compounds; or pharmaceutically acceptable alkali metal or acid addition salts thereof.

The most preferred compounds of the invention are those of Formula III

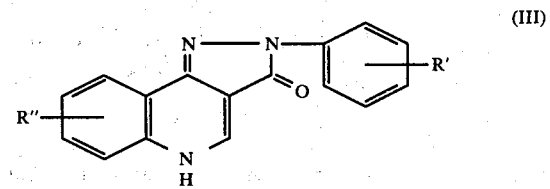

wherein R" is hydrogen, alkyl or alkoxy with up to 4 carbon atoms each, hydroxy, fluoro, chloro, bromo or trifluoromethyl; and R' is hydrogen, o- or m-fluoro; or it is p-fluoro when R" is chloro; or pharmaceutically acceptable alkali metal or acid addition salts thereof, for their predominant antidepressant activity.

The most preferred anxiolytic compounds of this invention are those of Formula III, wherein R" represents said substituents listed in the preceding paragraph; and R' is alkyl or alkoxy with up to 4 carbon atoms each, hydroxy, chloro, bromo, trifluoromethyl, nitro, amino, monoalkylamino or alkylcarbamoylamino with up to 4 carbon atoms each, or cyano; or it is p-fluoro when R" is different from chloro; or pharmaceutically acceptable alkali metal or acid addition salts thereof.

Outstanding on account of their antidepressant effects are the compounds of Formula III, wherein R" is hydrogen or 8-(methyl, methoxy, fluoro, or chloro), and R' is hydrogen; or it is 4-fluoro when R" is 8-chloro; or pharmaceutically acceptable alkali metal or acid addition salts thereof.

Outstanding on account of their anxiolytic effects are the compounds of Formula III, wherein R" is hydrogen or 8-(methyl, methoxy, fluoro or chloro), and R' is 4-(methyl, methoxy, chloro, bromo, amino or cyano); or it is 4-fluoro when R" is different from 8-chloro; or pharmaceutically acceptable alkali metal or acid addition salts thereof.

Special attention deserve the anti-depressant compounds of Formula III with R' being hydrogen; and R" being hydrogen, 8-(methoxy, fluoro or chloro), or R' being 4-fluoro and R" being 8-chloro; as well as the anxiolytic compounds of Formula II with R' being 4-(methyl, chloro or amino); and R" being hydrogen; or the sodium salt, hydrochloride or mesylate thereof.

The compounds of the invention are prepared according to conventional methods, for example by ring-closing:

(1) Compounds of Formula IV

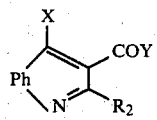

(IV)

wherein X is —NH—NH—R and Y is hydroxy or lower alkoxy; or X is halogen and Y is H₂N—N—R; or X is lower alkoxyamino or azido, and Y is NH—R; and, if desired, reacting a resulting compound, or an alkali metal salt thereof, with a reactive ester of the alcohol $R_1$—OH.

The ring-closure of said acids or esters IV occurs by heating them to temperatures between about 80° and 180°, advantageously in the presence of inert solvents, such as aliphatic or aromatic hydrocarbons and/or ethers, e.g. toluene, xylenes, biphenyls and/or diphenyl ethers, while distilling off the water or alkanols generated. Said hydrazides IV are similarly ring-closed, but advantageously under basic conditions, in order to neutralize the generated hydrohalic acids, for example in the presence of aqueous alkali metal hydroxides. The ring-closure of said amides IV occurs by heating them to temperatures between about 120° and 300°, preferably between 200° and 250°, advantageously also in the presence of said inert solvents.

Some of the starting material of Formula IV is new, but can easily be prepared from the known precursors with X=OH, e.g. as illustrated by the examples herein, or described in J. Med. Chem. 12, 1096 (1969) or C. R. Acad. Sc. Paris, t. 280, C, 1385 (1975), by condensation with corresponding aryl-hydrazines. Said hydrazides are prepared by condensing 4-chloroquinolin-3-carboxylic acid chlorides and β-acylated aryl-hydrazines, e.g. the trifluoroacetates, which hydrolyze under ring-closing conditions. Said amides are preferably obtained by condensing 4-haloquinolin-3-carboxylic acid halides with R-amines, and subsequently with 0-lower alkylhydroxylamines or alkali metal azides.

Another process for preparing the compounds of the invention consists in condensing compounds of Formula V

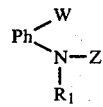

(V)

wherein both W and $R_1$ are hydrogen, Z is

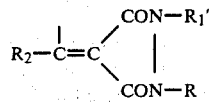

and $R_1'$ is lower alkyl; or W is

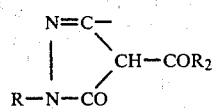

and Z is hydrogen; or W is

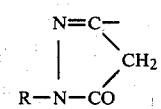

and Z is $R_2$—CO, or $R_1$—N—Z together is isocyano; and, if desired, converting any resulting compound of Formula I into another compound of the invention.

Said ring-closing condensation of the W=H compounds is preferably carried out with strong aprotic condensation agents, such as polyphosphoric acid lower alkyl esters. In case the compounds with Z=H are ring-closed, the water generated is advantageously removed azeotropically, preferably in said hydrocarbons and/or ethers, if desired, in the presence of conventional molecular sieves, and/or a catalytic amount of acid, e.g. hydrochloric acid.

Lastly, compounds V with carbon containing W and Z are ring-closed under basic conditions, e.g. in the presence of said aqueous alkali metal hydroxides, or tertiary organic amines, such as tri-lower alkylamines.

The starting material of Formula V is also new, but can be prepared according to known methods, e.g. by condensing an 1-aryl-pyrazolidin-3,5-dione with ethyl orthoformate and an aniline. Said second starting material V can be prepared analogous to the process described in Izv. Akad. Nauk. Latv. S.S.R. 1965, 587, but chosing analogs with an o-nitro group, which is subsequently reduced with catalytically activated hydrogen. Said final starting material V is similarly prepared from said common 1-R-3-(o-nitrophenyl)-5-pyrazolones, by reducing, N-acylating and, if desired, dehydrating them to said isonitriles with phosphorus halides or oxyhalides.

The resulting compounds of the invention can be converted into each other according to conventional methods. For example, compounds with $R_1$=H can be 1-substituted with reactive esters of $R_1$—OH, e.g. such of hydrohalic, aliphatic or aromatic sulfonic acids, such as $R_1$-(halides, sulfates, aliphatic or aromatic sulfonates), e.g. methyl iodide, dimethyl sulfate, benzyl chloride or methyl mesylate or tosylate, in order to yield the 1-substituted compounds of Formula I. Those of Formula II are similarly obtained from the corresponding alkali metal salts, e.g. with $R_1$ being sodium or potassium, whereby 5-substitution occurs. Furthermore, resulting lower alkoxy compounds may be hydrolyzed to the corresponding phenols with strong hydrohalic acids, e.g. hydrobromic acid. Resulting nitro compounds may be hydrogenated to the corresponding amines with catalytically activated or nascent hydrogen, e.g. hydrogen in the presence of noble metal catalysts, such as nickel, palladium or platinum; or generated by the action of reactive metals on alcohols or acids, such as zinc or hydrohalic acids. Said amines may be alkylated as shown for the componds with $R_1$=H, or by reductive alkylation; or acylated, for example, with the use of corresponding reactive acid derivatives, e.g. anhydrides, halides or isocyanates.

Finally, a resulting compound can either be converted into its alkali metal salts, advantageously with the use of alkali metal hydrides, hydroxides or lower alkoxides; or into its acid addition salts (especially if amino-substituted compounds are involved), preferably with the use of pharmaceutically acceptable inorganic or organic acids, such as strong metalloidic acids, for example, hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic tartaric, citric, ascorbic, maleic, hydroxymaleic, pyruvic, phenylacetic, benzoic, 4-aminobenzoic, anthranilic, 4-hydroxybenzoic, salicylic, 4-aminosalicylic, embonic, nicotinic; methanesulfonic, ethane-sulfonic, hydroxyethanesulfonic, ethylenesulfonic; halogenobenzene sulfonic, toluenesulfonic, naphthalenesulfonic, sulfanilic or cyclohexylsulfamic acid. These or other salts, for example the picrates, can also be used for purification of the amino-bases obtained; these are converted into salts, the salts are separated and the free compounds liberated from the salts. In view of the close relationship between the free compounds and the compounds in the form of their salts, whenever a compound is referred to in this context, a corresponding salt is also intended, provided such is possible or appropriate under the circumstances. Acid addition salts of compounds devoid of basic substituents, e.g. an amino group, usually hydrolyse in about neutral aqueous media.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

Resulting mixtures of isomers can be separated into the single isomers by methods in themselves known, e.g. by fractional distillation, crystallization and/or chromoatography.

The invention further includes any variant of the above processes in which an intermediate product, obtainable at any stage thereof is used as starting material, and any remaining steps are carried out, or said process is discontinued at any stage thereof, or in which the starting materials are formed under the reaction conditions, e.g. those of Formula IV with X=NH—NH—R, from their precursors with X=Cl, or in which the reaction components are used in the form of their salts. Mainly those starting materials should be used in the reactions of the invention that lead to the formation of those compounds indicated above as being especially valuable, e.g. those of Formula III.

The pharmacologically active compounds of the invention are useful in the manufacture of pharmaceutical compositions containing an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethylene-glycol, for tablets also (c) binders, e.g. magnesium aluminum silicate, starch paste, gelatin, tragacanth, methylcellulose, sodium carboxymethyl-cellulose and/or polyvinylpyrrolidone, if desired, (d) disintegrants, e.g. starches, agar, alginic acid or its sodium salt, enzymes of the binders, or effervescent mixtures and/or (e) absorbents, colorants, flavors and sweeteners. Injectable compositions are preferably aqueous isotonic solutions or suspensions, and suppositories are advantageously made from fatty emulsions or suspensions. They may be sterilized and/or contain adjuvants, such as preserving, stabilizing, wetting or emulsifying agents, solution promoters, salts for regulating the osomotic pressure and/or buffers. They may also contain other therapeutically valulable substances. Said pharmaceutical compositions are prepared according to conventional mixing, granulating or coating methods respectively and contain about 0.1 to 75%, preferably about 1 to 50% of the active ingredient.

The following examples, illustrating the invention, are not to be construed as being limitations thereon. Temperatures are given in degrees Centigrade, all parts wherever given are parts by weight and, if not otherwise stated, all evaporations are carried out under reduced pressure, e.g. between about 0.1 and 15 mmHg.

EXAMPLE 1

The mixture of 1,681 g of ethyl 4-chloro-quinoline-3-carboxylate, 1,017 g of p-chlorophenylhydrazine and 25 L of xylene is heated to 105° for 24 hours while stirring under nitrogen. The resulting suspension is cooled to 20°, combined with 14 L of 2 N aqueous sodium hydroxide, stirred for 15 minutes and diluted with 30 L of water. Stirring is continued for 1 hour, the aqueous phase separated, washed five times with 8 L of diethyl ether each, filtered and the filtrate treated with the solution of 1,600 g of ammonium chloride in 8 L of water while stirring under nitrogen. The resulting suspension is stirred overnight at room temperature, filtered and the residue washed 5 times with 12 L of hot water. This residue is dried at 5 mmHg and 90° and 1,665 g thereof are dissolved in 8.4 L of dimethylformamide at 130°. The solution is filtered and allowed to cool to room temperature while stirring. The resulting suspension is filtered, washed twice with 500 ml of cold dimethylformamide each, four times with 1 L of diethyl ether and the residue is dried at 0.1 mmHg and 100°, to yield the 2-(p-chlorophenyl)-pyrazolo[4,3-c]quinolin-3(5H)-one of the formula

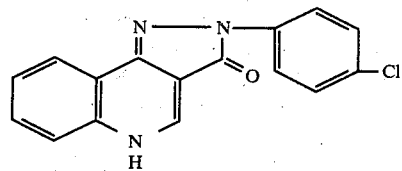

melting at 324°–327° with decomposition.

The starting material is prepared according to the following (generally applicable) method: To 1,272 g of aniline, 2, 953 g of diethyl ethoxymethylenemalonate are added during 20 minutes while stirring, and stirring is continued for 135 minutes at 90°–92°. Thereafter the generated ethanol is distilled off during 4 hours at 10 mmHg and 80°. The residual oil is allowed to crystallize on trays, it is pulverized and dried at 5 mmHg and room temperature to yield the diethyl phenylaminomethylenemalonate melting at 45°–46°.

1,085 g thereof are added during 45 minutes to 10.850 ml of the eutectic diphenyl ether-biphenyl mixture (73.5:26.5 parts by weight) at 215°–220°, while stirring under nitrogen. After completed addition the temperature is raised to 238° and the generated mixture of ethanol and diphenyl ether is collected in a trap during 4 hours (about 390 ml). The mixture is allowed to cool to room temperature while stirring, the resulting suspension is filtered, the residue washed twice with 500 ml of diethyl ether each and dried at 0.1 mmHg and 85°, to yield the ethyl 4-hydroxyquinolin-3-carboxylate melting at 276°–280°.

1,630 g thereof are added to 2,463 ml of phosphorus oxychloride during 30 minutes while stirring under nitrogen. The mixture is stirred for 15 minutes at 70° and for 2 hours at 95°, whereupon the liquid is distilled off at 11 mm Hg and 60°. The residue is dissolved in 8 L of methylene chloride, the solution is cooled to 0° and treated with 5,000 g of crushed ice. The mixture is stirred, combined with 3 L of 50% aqueous sodium hydroxide below 15°, and when the pH=12 is reached the organic layer is separated. It is washed twice with 2 L of water each, once with 2 L of saturated aqueous sodium chloride, dried and evaporated. The residual oil is allowed to crystallize on trays, it is pulverized and dried at 0.1 mmHg and room temperature, to yield the ethyl 4-chloro-quinolin-3-carboxylate melting at 44°–46°.

To the solution of 1,445 g of p-chloroaniline in 3,375 ml of 38% hydrochloric acid and 5,650 ml of water the solution of 793 g of sodium nitrite in 3.3 L of water is added during 1 hour at −5° to −8° while stirring under nitrogen. After 15 minutes 7,617 g of stannous chloride in 9 L of 38% hydrochloric acid are added during 30 minutes below 25°. The resulting suspension is stirred in an ice bath for one hour, filtered, the residue suspended in 30 L of water, and 5,000 g of solid sodium hydroxide are added during 1 hour at 0°–25°, while stirring under nitrogen. The mixture is extracted twice with 8 L of diethyl ether, the combined extracts washed twice with 4 L of water and once with saturated aqueous sodium chloride, dried, filtered, evaporated and the residue dried at 5 mmHg and room temperature, to yield the p-chlorophenyl-hydrazine melting at 82°–87°.

EXAMPLE 2

The mixture of 1.00 g of 2-(p-chlorophenyl)-pyrazolo[4,3-c]quinolin-3(5H)-one and 3.38 ml of N aqueous sodium hydroxide is stirred under nitrogen at room temperature overnight. The resulting solution is filtered, evaporated and the residue dried under reduced pressure, to yield the corresponding sodium salt melting at 280°–284°.

EXAMPLE 3

The mixture of 1.00 g of 2-(p-chlorophenyl)-pyrazolo-[4,3-c]quinolin-3(5H)-one, 20 ml of trifluoroacetic acid and 0.325 g of methanesulfonic acid is stirred at room temperature for 1 hour and evaporated. The residue is triturated with diethyl ether and filtered off, to yield the corresponding mesylate melting at 250°–255°.

EXAMPLE 4

The mixture of 3.0 g of 2-(p-chlorophenyl)-pyrazolo[4,3-c]quinolin-3(5H)-one and 100 ml of dimethyl sulfate is stirred at 110°–130° for 2 hours and evaporated. The residue is dissolved in N aqueous sodium hydroxide, the solution extracted with methylene chloride and the extract evaporated. The residue is recrystallized from diethyl ether, to yield the 1-methyl-2-(p-chlorophenyl)-pyrazolo[4,3-c]quinolin-3-one melting at 158°–161°.

EXAMPLE 5

The mixture of 5.0 g of 2-(p-chlorophenyl)-pyrazolo[4,3-c]quinolin-3(5H)-one, 0.81 g of 50% sodium hydride in mineral oil and 100 ml of anhydrous tetrahydrofuran is refluxed for 2 hours. It is cooled to room temperature, combined with 3.0 g of methyl iodide while stirring and another 1.0 g thereof is added after one hour. The mixture is stirred overnight at room temperature, filtered and the residue recrystallized from tetrahydrofuran-heptane, to yield the 5-methyl-2-(p-chlorophenyl)-pyrazolo[4,3-c]quinolin-3-one melting at 322°–323°.

EXAMPLE 6

The mixture of 10.0 g of 2-(p-chlorophenyl)-pyrazolo-[4,3-c]quinolin-3(5H)-one, 1.8 g of 50% sodium hydride in mineral oil and 250 ml of 1,2-dimethoxyethane is stirred at 100° until dissolution. It is cooled to room temperature and 15.0 g of 3-dimethylaminopropyl chloride in 10 ml of 1,2-dimethoxyethane are added. The mixture is stirred at 150° overnight, cooled, the supernatant solution decanted off and the residue treated with said solvent, to yield the 5-(3-dimethylaminopropyl)-2-(p-chlorophenyl)-pyrazolo-[4-3-c]quinolin-3-one melting at 189°–191°. Similarly the 5-(2-dimethylaminoethyl)-analog is obtained, m.p. 184°–186°.

EXAMPLE 7

The mixture of 2.0 g of 2-(p-chlorophenyl)-pyrazolol-[4,3-c]quinolin-3(5H)-one, 0.33 g of 50% sodium hydride in mineral oil and 50 ml of 1,2-dimethoxyethane is stirred at 100° until dissolution. It is cooled to room temperature, combined with 3.9 g of o-fluorobenzyl chloride in 2 ml of 1,2-dimethoxyethane and the mixture refluxed for 4 hours. It is cooled to room temperature, filtered, the residue washed with diethyl ether, slurried in 10 ml of N aqueous sodium hydroxide, filtered again, washed with water and dried, to yield the 5-(o-fluorobenzyl)-2-(p-chlorophenyl)-pyrazolo-[4,3-c]quinolin-3-one melting at 338°–339°.

EXAMPLE 8

The mixture of 3.5 g of ethyl 4-(2,4-dichlorophenyl-hydrazino)-quinolin-3-carboxylate and 40 ml of eutectic diphenyl ether-biphenyl is heated to 175° for 4 hours, cooled to room temperature and diluted with diethyl ether. The resulting suspension is filtered, the residue washed with diethyl ether and dissolved in N aqueous sodium hydroxide. The solution is washed with diethyl ether, its pH adjusted to 8.5 with ammonium chloride and the precipitate formed collected. It is washed successively with hot water, methanol and diethyl ether, to yield the 2-(2,4-dichlorophenyl)-pyrazolo[4,3-c]-quinolin-3(5H)-one, showing peaks in the IR-spectrum at 890, 867, 845, 832, 816, 796, 775, 767, 756, 730 and 701 cm$^{-1}$.

The starting material is prepared as follows. The mixture of 2.8 g of ethyl 4-chloroquinolin-3-carboxylate, 2.1 g of 2,4-dichlorophenylhydrazine and 40 ml of eutectic diphenyl ether-biphenyl is heated to 80°–90° overnight while stirring. It is cooled to room temperature, diluted with diethyl ether and the precipitate collected. It is taken up in N aqueous sodium hydroxide, the solution extracted with diethyl ether, the extract washed with water, dried, filtered, concentrated and the precipitate collected, to yield the ethyl 4-(2,4-dichlorophenyl hydrazine)quinolin-3-carboxylate, melting at 151°–153°.

EXAMPLE 9

The mixture of 3.6 g of ethyl 4-chloro-2-methylquinolin-3-carboxylate, 1.8 g of phenylhydrazine and 40 ml of xylene is refluxed for 4 hours, cooled to room temperature, diluted with diethyl ether and filtered. The residue is dissolved in 50 ml of 2 N aqueous sodium hydroxide, the solution washed with diethyl ether and its pH adjusted to 8.5 with ammonium chloride. The precipitate formed is collected, washed successively with hot water, methanol and diethyl ether, to yield the 4-methyl-2-phenylpyrazolo[4,3-c]quinolin-3(5H)-one, showing in the IR-spectrum peaks at 874, 867, 858, 850, 822, 780, 765, 756, 750, 740 and 722 cm$^{-1}$. Analogously the 4-methyl-2-(p-chlorophenyl)-pyrazolo[4-3,-c]quinolin-3(5H)-one is prepared, melting at 349°–350°.

EXAMPLE 10

The mixture of 2.7 g of ethyl 4-chloro-6-methoxyquinolin-3-carboxylate, 1.4 g of p-fluorophenylhydrazine and 20 ml of eutectic diphenyl ether-biphenyl is heated to 160°–165° for 4 hours, then cooled to room temperature and diluted with diethyl ether. The precipitated crystalline product is collected, washed thoroughly with diethyl ether and dried, to yield the 2-(p-fluorophenyl)-8-methoxypyrazolo]4,3-c]quinolin-3(5H)-one hydrochloride melting at 322°–324°.

EXAMPLE 11

The mixture of 4.0 g of ethyl 4-chloroquinolin-3-carboxylate, 2.04 g of 2-hydrazinopyridine and 50 ml of eutectic diphenyl ether-biphenyl is stirred at 110°–130° for 3 hours under nitrogen. After cooling to room temperature it is diluted with diethyl ether, filtered, the solids washed with diethyl ether and dissolved in 100 ml of aqueous sodium hydroxide. The solution is washed with diethyl ether and the pH thereof adjusted to 8.5 by addition of ammonium chloride. The precipitate formed is collected, washed successively with water, methanol and diethyl ether, to yield the 2-(2-pyridyl)-pyrazolo[4,3-c]quinolin-3(5H)-one showing in the IR-spectrum peaks at 887, 865, 853, 788, 780, 765, 756, 737 and 726 cm$^{-1}$.

Analogously the corresponding 8-fluoro-analog is prepared, showing IR-peaks at 895, 868, 826, 792, 776, 758 and 725 cm$^{-1}$.

The starting material for the latter is prepared as follows: The mixture of 28.9 g of ethyl 6-fluoro-4-hydroxy-quinolin-3-carboxylate [J.A.C.S., 69, 371 (1947)] and 240 ml of phosphorus oxychloride is refluxed under nitrogen for 3 hours. After cooling to room temperature, the solution is evaporated and the residue treated with ice-water and chloroform. The organic layer is dried and evaporated. The residue is taken up in aqueous sodium bicarbonate and diethyl ether, the ethereal layer is dried and evaporated, to yield the ethyl 4-chloro-6-fluoroquinolin-3-carboxylate melting at 55°–57°.

EXAMPLE 12

The mixture of 3.0 g of 2-(p-methoxyphenyl)-pyrazolo-[4,3-c]quinolin-3(5H)-one and 260 ml of 48% hydrobromic acid is refluxed for 1 hour and concentrated to about 50 ml. The concentrate is cooled to room temperature, the precipitate collected, washed with methanol and diethyl ether, and dissolved in diluted aqueous sodium hydroxide. The solution is washed with diethyl ether, then its pH adjusted to 8.5 by addition of ammonium chloride, precipitating a solid which is collected, washed with methanol, then with diethyl ether and dried, to yield the 2-(p-hydroxyphenyl)-pyrazolo[4,3-c]quinolin-3(5H)-one melting at 294°–296°.

EXAMPLE 13

The solution of 1.9 g of 2-(p-nitrophenyl)-pyrazolo-[4,3-c]-quinolin-3(5H)-one in the mixture of 18.6 ml of 2 N aqueous sodium hydroxide and 75 ml of ethanol is hydrogenated over 0.2 g of platinum oxide at 2.7 atm. for 6 hours. The mixture is filtered, the filtrate evaporated; the residue taken up in water and the solution washed with diethyl ether. The pH thereof is adjusted to about 8.5 by addition of aqueous ammonium chloride, the precipitate collected, washed successively with methanol and diethyl ether and dried, to yield the 2-(p-aminophenyl)-pyrazolo[4,3-c]quinolin-3(5H)-one, showing IR-peaks at 896, 885, 865, 840, 820, 815, 782, 776, 761, 740, 736 and 720 cm$^{-1}$.

EXAMPLE 14

To the mixture of 1.4 g of 2-(p-aminophenyl)-pyrazolo-[4,3-c]quinolin-3(5H)-one, 4.1 ml of 37% aqueous formaldehyde, 1.0 g of sodium cyanoborohydride and 20 ml of acetonitrile, 0.6 g of glacial acetic acid are added while stirring. Stirring is continued overnight at room temperature and the mixture diluted with water. The precipitate formed is dissolved in diluted sodium hydroxide, the aqueous solution washed with diethyl ether and its pH adjusted to 8.5 by addition of aqueous ammonium chloride. The precipitate formed is collected, washed with methanol, then with diethyl ether and dried to yield the 2-(p-methylaminophenyl)-pyrazolo[4,3-c]quinolin-3(5H)-one melting at 302°–304°.

EXAMPLE 15

The mixture of 0.7 g of 2-(p-aminophenyl)-pyrazolo[4,3-c]quinolin-3(5H)-one, 1.4 g of methylisocyanate and 25 ml of methanol is refluxed for 7 hours and allowed to stand at room temperature overnight. It is evaporated, the residue treated with diluted aqueous sodium hydroxide and diethyl ether, the aqueous solution separated, washed with diethyl ether and its pH adjusted to 8.5 with ammonium chloride. The precipitate formed is collected, washed with methanol, then with diethyl ether and dried, to yield the 2-(p-methylcarbamoylaminophenyl)-pyrazolo[4,3-c]quinolin3(5H)-one, showing IR-peaks of 895, 869, 850, 825, 816, 812, 785, 780, 767 and 738 cm$^{-1}$.

EXAMPLE 16

38.5 ml of a 0.17 M solution of ethyl 4-chloroquinoline-3-carboxylate in xylene, and 0.96 g of p-cyanophenylhydrazine in 30 ml of xylene are mixed and heated at 115° to 120° for 3 hours. The mixture is then cooled to room temperature, and stirred with 20 ml of 1 N aqueous sodium hydroxide and sufficient water to dissolve all solids. The aqueous layer is separated, washed twice with diethyl ether, then treated with an aqueous solution of 1.07 g ammonium chloride, and the resulting precipitate is collected, washed with water and dried to yield the 2-(p-cyanophenyl)-pyrazolo[4,3- c]quinolin-3(5H)-one, showing peaks in the IR-spectrum at 885, 830, 780, 755 and 730 cm$^{-1}$.

EXAMPLE 17

One gram of 2-(p-cyanophenyl)-pyrazolo[4,3-c]quinolin-3(5H)-one, 3.50 ml of 1 N aqueous sodium hydroxide and 10 ml of ethanol are mixed and stirred at room temperature until the solid has dissolved. The solution is then treated with 1.4 ml of 30% hydrogen peroxide, giving an immediate precipitate. After stirring for 2 hours at room temperature, the mixture is filtered, and the solid is crystallized from dimethylformamide, to yield the 2-(p-carbamoylphenyl)-pyrazolo [4,3-c]quinolin-3(5H)-one, showing peaks in the IR-spectrum at 885, 853, 830, 785, 775, 752 and 732 cm$^{-1}$.

EXAMPLE 18

One gram of 2-(p-cyanophenyl)-pyrazolo[4,3-c]quinolin-3(5H)-one and 50 ml of 2 N aqueous sodium hydroxide are mixed and refluxed for 3 hours. The solution is acidified with 50 ml of hydrochloric acid, filtered, and the collected precipitate dried. It is taken up in 25 ml of 1 N aqueous sodium hydroxide, and the solution neutralized to pH=6–7 with 1 N hydrochloric acid. The resulting solid is filtered off, triturated with water and dried, to give the 2-(p-carboxyphenyl)-pyrazolo[4,3-c]quinolin-3(5H)-one 3/2 hydrate, showing IR-peaks at 886, 858, 820, 780, 770, 760 and 730 cm$^{-1}$.

EXAMPLE 19

The pH of the solution of 1.0 g of 4-chloroquinoline-3-(N-phenyl-N-trifluoroacetamido)carboxamide in the minimum amount of 50% aqueous tetrahydrofuran is adjusted to 10 by the addition of lithium hydroxide. The mixture is stirred at room temperature for 48 hours, concentrated to remove most of the tetrahydrofuran, washed with dichloromethane, and acidified to pH=3 by addition of diluted hydrochloric acid. The precipitate formed is collected by suction filtration, and purified by preparative thin layer chromatography using toluene: ethanol: conc. ammonium hydroxide (70:30:3) as developing solvent on silica gel, to obtain the 2-phenyl-pyrazolo[4, 3-c]quinolin-3(5H)-one melting at 326°–328°.

The starting material is prepared as follows: To the ice-cooled solution of 10.8 g of phenylhydrazine in 120 ml of diethyl ether, 10.5 g of trifluoroacetic anhydride in 25 ml of diethyl ether are added dropwise over the period of 15 minutes. The mixture is stirred at 0°–5° for 15 minutes, then at room temperature for 2 hours, whereupon it is filtered. The filtrate is washed with water, dried, evaporated and the residue crystallized from diethyl ether: n-heptane, to yield the β-trifluoroacetylphenylhydrazine melting at 119°–121°.

The mixture of 1.5 g thereof, is stirred in 100 ml of tetrahydrofuran with 0.06 g of lithium hydride under moisture exclusion for 5 hours at room temperature, to form a solution. Separately, 1.9 g of 4-chloro-3-chlorocarbonylquinoline hydrochloride are stirred in 100 ml of tetrahydrofuran with 0.06 g of lithium hydride under moisture exclusion for one minute at 10°, and the solution is added to the former in 10 ml portions. The mixture is stirred at room temperature for 18 hours, then refluxed for 8 hours and concentrated under reduced pressure, obtaining the 4-chloroquinoline-3-(N-phenyl-N-trifluoroacetamido)-carboxamide, which is used without further purification.

EXAMPLE 20

The mixture of 0.211 g of 4-(O-methylhydroxylamino)-quinoline-3-(N-p-chlorophenyl)-carboxamide, and 15 ml of eutectic diphenyl ether-diphenyl is heated to 240° for 2 hours under nitrogen. It is cooled to room temperature, diluted with 150 ml of petroleum ether, and the resultant precipitate is collected. It is washed with petroleum ether, stirred with 15 ml of diethyl ether and 3 ml of 2 N aqueous sodium hydroxide for 1 hour, filtered to remove insoluble material, and the layers of the filtrate are separated. The aqueous phase is treated with 0.32 g of ammonium chloride, to give a yellow precipitate, which is collected and recrystallized from ethanol, to yield the 2-(p-chlorophenyl)-pyrazolo[4,3-c]quinolin-3(5H)-one melting at 327°; it is identical with that of Example 1.

The starting material is prepared as follows: The mixture of 11.62 g of 4-hydroxyquinoline-3-carboxylic acid [M. Hamana et al., Chem. Pharm. Bull., 26, 3856 (1978)], 7.84 g of p-chloroaniline, 17.59 g of 1-ethoxycarbonyl-2-ethoxy-1,2-dihydroquinoline, and 150 ml of dimethylformamide is heated at 60°–70° for 2 hours, to obtain a clear solution. It is cooled, filtered and evaporated in a rotary evaporator. The residue is triturated with diethyl ether, filtered, and the collected solid is washed with diethyl ether, to yield a mixture containing starting acid. It is stirred in 100 ml of 2 N aqueous sodium hydroxide for 1.5 hour, filtered, washed with water, and dried to obtain the 4-hydroxyquinoline-3-(N-p-chlorophenyl)-carboxamide, showing IR-peaks at 3450, 3260 and 3210 cm$^{-1}$.

The mixture of 1.0 g thereof and 25 ml of phosphorus oxychloride is heated at 80° for 3 hours to obtain a clear solution. It is evaporated, the residue treated with 400 ml of a 1:1 mixture of ice and 2 N aqueous sodium hydroxide, stirred with 200 ml of dichloromethane, filtered and the layers separated. The organic phase is dried and evaporated, to yield the 4-chloroquinoline-3-(n-p-chlorophenyl)-carboxamide, melting at 229°–234°. (It may also be prepared by treating said acid with phosphorus oxychloride first, and the resulting dichloride with said aniline second).

The mixture of 0.5 g thereof, 1.0 g of O-methylhydroxylamine hydrochloride and 1.65 g of diisopropylethylamine is heated to 100° in a small pressure vessel for 18 hours. The cooled mixture is then triturated with water, dissolved in tetrahydrofuran, dried, evaporated and the residue recrystallized from methanol, to yield the 4-(O-methylhydroxylamino)-quinoline-3-(N-chlorophenyl)-carboxamide melting at 210°–212°.

EXAMPLE 21

The solution of 308 mg of 1-(p-chlorophenyl)-4-hydroxymethylene-3-(o-nitrophenyl)-4,5-dihydropyrazol-5-one in 80 ml of tetrahydrofuran is hydrogenated over 50 mg of 5% platinum on charcoal at room temperature and 3 atmospheres for 0.5 hour. The mixture is filtered, the filtrate evaporated and the residue taken up in 150 ml of toluene. To the solution, 0.1 ml of conc. hydrochloric acid is added, and the mixture refluxed at a water separator for 18 hours. It is cooled, the precipitate formed filtered off and purified by preparative thin layer chromotography, using ethyl acetate:ethanol:conc. ammonium hydroxide (17:3:3) as developing solvent on silica gel, to yield the 2-(p-chlorophenyl)-pyrazolo[4, 3-c]quinolin-3(5H)-one melting at 327°, it is identical with that of Example 1.

The starting material is prepared as follows: The solution of 39.6 g of monoethyl malonate, 50 mg of 2,2-bipyridyl (indicator) and 650 ml of tetrahydrofuran is cooled to −70°, whereupon 305 ml of 1.97 M n-butyl lithium in hexane are added slowly under nitrogen while stirring. The temperature is allowed to rise to about −5° near the end of addition, after the pink color of the indicator persists. The mixture is recooled to −65°, and the solution of 31.7 g of o-nitrobenzoyl chloride in 50 ml of tetrahydrofuran is added dropwise within 10 minutes. The resultant mixture is stirred at room temperature for 1 hour and then poured onto a mixture of 650 ml of 1 N hydrochloric acid and 1100 ml of diethyl ether. The organic layer is separated, washed successively with 350 ml of saturated aqueous sodium bicarbonate, 400 ml of water and 200 ml of brine, dried and evaporated, to yield the ethyl 2-(o-nitrobenzoyl)-acetate, as an oil.

The solution of 3.55 g thereof and 1.7 g of p-chlorophenylhydrazine in 65 ml of toluene is refluxed for 3 hours at a water separator. The mixture is evaporated, the residue chromotographed on silica gel with 15% ethyl acetate in toluene as eluent, to yield the 1-(p-chlorophenyl)-3-(o-nitrophenyl)-4,5-dihydropyrazol-5-one, melting at 138°–141°.

0.7 g thereof is stirred in 10 ml of dimethylformamide dimethylacetal at room temperature for 18 hours. The dark reaction mixture is poured onto ice-water, the precipitate is collected by suction filtration, taken up in ethyl acetate, washed with water, dried and evaporated to leave the 1-(p-chlorophenyl)-4-dimethylaminomethylene-3-o-nitrophenyl-4,5-dihydropyrazol-5-one, melting at 208°–210° (dec.).

2.5 g thereof are stirred in the mixture of 20 ml of tetrahydrofuran and 20 ml of 20% aqueous hydrochloric acid, at 60° for 3 hours, then at room temperature for 18 hours. It is diluted with brine, the precipitate collected and washed with ethyl acetate, leaving the 1-(p-chlorophenyl)-4-hydroxymethylene-3-(o-nitrophenyl)-4,5-dihydropyrazol-5-one, melting at 155°–157°.

EXAMPLE 22

The mixture of 650 mg of 1-(p-chlorophenyl)-2-methyl-4-anilinomethylidene-pyrazolidin-3,5-dione, 2.0 g of ethyl polyphosphate and 10 ml of 1,1,2,2-tetrachloroethane is refluxed for 24 hours. The solution is poured onto 10 ml of 2 N aqueous sodium hydroxide and the organic layer chromatographed on silica gel plates, using toluene:ethanol:conc. ammonium hydroxide (80:20:1) as eluent, to yield the 2-(p-chlorophenyl)-1-methyl-pyrazolo[4,3-c]quinolin-3-one with an Rf=0.48. When using dichloromethane:methanol (19:1) as eluent, said compound has the Rf=0.33; it is identical with that of Example 4.

The starting material is prepared as follows: 20.0 g of diethyl malonate are added to 5.8 g of sodium metal dissolved in 100 ml of absolute ethanol. After stirring for 15 minutes, 17.8 g of p-chlorophenylhydrazine are added, and the resulting mixture is stripped to remove excess ethanol. The residue is heated at 110° to 120° for 4.5 hours, then quenched with 500 ml of ice-water. The resulting mixture is washed twice with diethyl ether and the aqueous layer is acidified with conc. hydrochloric acid to a pH below 2. The resulting solid is recrystallized from toluene, to give the 1-(p-chlorophenyl)-pyrazolidin-3,5-dione melting at 189°–193°.

The mixture of 2.0 g thereof, 2.81 g of triethyl orthoformate, 0.97 g of aniline and 30 ml of ethanol is refluxed for 16 hours. It is cooled, filtered and washed, to yield the 1-(p-chlorophenyl)-4-anilinomethylidenepyrazolidin-3,5-dione, melting at 288°–290°.

The mixture of 500 mg thereof, 15 mg of lithium hydride and 2.0 ml of dimethylformamide is heated at 70° for 3 hours. The solution is then cooled to 5°, and 700 mg of methyl iodide are added. The mixture is stirred for 16 hours at room temperature and evaporated. The residue is taken up in water and dichloromethane, the organic phase separated, dried and evaporated, to yield the 1-(p-chlorophenyl)-2-methyl-4-anilinomethylidenepyrazolidin-3,5-dione, showing NMR-peaks at 3.14, 7.47, 8.42, 10.92 and 10.98 ppm.

EXAMPLE 23

The solution of 50 mg of 1-(p-chlorophenyl)-3-(o-formylaminophenyl)-4,5-dihydropyrazol-5-one in 10 ml of dichloromethane is evaporated, leaving a thin film on the flask wall. This is heated at 190°–200° for 30 minutes under a gentle stream of nitrogen. The reaction product is chromatographed on silica gel plates, using ethyl acetate:ethanol:conc. ammonium hydroxide (17:3:3) as eluent, to yield the 2-(p-chlorophenyl)-pyrazolo[4,3-c]quinolin-3(5H)-one with an Rf=0.16. When using 5% methanol in dichloromethane, said compound has the Rf=0.07, and with toluene:ethanol:conc. ammonium hydroxide (70:30:3), the Rf=0.32.

The starting material is prepared thus: 2 g if 1-(p-chlorophenyl)-3-(o-nitrophenyl)-4,5-dihydropyrazol-5-one are catalytically hodrogenated in 100 ml of ethanol over 200 mg of 5% platinum on carbon at room temperature and 3 atmospheres. Since the product crystallizes from the mixture as it is formed, the mixture is diluted with dichloromethane to dissolve said crystalline product. It is filtered, the filtrate evaporated, and the dried residue recrystallized from ethanol, affording the 3-(o-aminophenyl)-1-(p-chlorophenyl)-4,5-dihydropyrazol-5-one melting at 199°–201°.

0.3 g thereof are added to 10 ml of 97% formic acid under ice cooling while stirring under nitrogen, to give a colorless solution. 1 ml of acetic anhydride is added and the mixture stirred overnight at room temperature, then poured into 300 ml of brine. The white precipitate is collected, dissolved in 200 ml of diethyl ether, dried and evaporated, leaving the 1-(p-chlorophenyl)-3-(o-formylaminophenyl)-4,5-dihydropyrazol-5-one, melting at 170°–172°.

EXAMPLE 24

According to the methods illustrated by the previous examples, advantageously Examples 1 and 8–11, the following compounds of Formula II are prepared: $R_1=R_2=H$.

| No. | Ph | R | m.p. °C. or IR-peaks cm$^{-1}$ |
|---|---|---|---|
| 1 | 8-CH$_3$O—C$_6$H$_3$ | 2-pyridyl | 319–323 |
| 2 | 7-CF$_3$—C$_6$H$_3$ | 2-pyridyl | 348–350 |
| 3 | C$_6$H$_4$ | 4-CH$_3$—2-pyridyl | 342–344 |
| 4 | C$_6$H$_4$ | 5-Cl—2-pyridyl | 886,835,828,797,778,756 |
| 5 | C$_6$H$_4$ | 2,5-Cl$_2$—phenyl | 337–338 |
| 6 | C$_6$H$_4$ | 3,4-Cl$_2$—phenyl | 890,878,867,823,818,795 |
| 7 | C$_6$H$_4$ | 3,5-Cl$_2$—phenyl | 890,871,847,830,806,788 |

As well as compounds of Formula III:

| No. | R″ | R′ | m.p. °C. or IR-peaks cm$^{-1}$ |
|---|---|---|---|
| 8 | H | o-CH$_3$ | 349–350 (HCl-salt) |
| 9 | H | p-CH$_3$ | 338–340 |
| 10 | H | p-OCH$_3$ | 268–270 |
| 11 | | p-SCH$_3$ | 307–309 |
| 12 | H | p-F | 342–346 |
| 13 | H | m-F | 335–338 |
| 14 | H | o-F | 338–340 |
| 15 | H | o-Cl | 336–339 |
| 16 | H | m-Cl | 336–337 |
| 17 | H | p-Br | 328–330 |
| 18 | H | p-CF$_3$ | 315–320 |
| 19 | H | p-NO$_2$ | 886,853,818,780,758,749 |
| 20 | 7-Cl | H | 872,851,830,818,798,770 |
| 21 | 7-Cl | p-Cl | 865,852,823,795,768,752 |
| 22 | 7-Cl | p-F | 890,858,835,804,770,731 |
| 23 | 7-Cl | m-Cl | 333–335 |
| 24 | 8-CH$_3$ | H | 860,810,785,770,750,730 |
| 25 | 8-CH$_3$ | p-CH$_3$ | 340–342 |
| 26 | 8-CH$_3$ | p-Cl | 335–337 |
| 27 | 8-OCH$_3$ | H | 321–325 |
| 28 | 8-OCH$_3$ | p-OCH$_3$ | 313–315 |
| 29 | 8-OCH$_3$ | o-F | 344–347 |
| 30 | 8-OCH$_3$ | m-Cl | 324–327 |
| 31 | 8-OCH$_3$ | p-Cl | 347–349 |
| 32 | 8-F | H | 327–328 |
| 33 | 8-F | p-OCH$_3$ | 289–292 |
| 34 | 8-F | p-F | 884,868,827,767,715,708 |
| 35 | 8-F | m-F | 900,881,865,839,827,774 |
| 36 | 8-F | o-F | 868,850,815,782,750,724 |
| 37 | 8-F | p-Cl | 342–345 |
| 38 | 8-F | m-Cl | 870,810,800,775,760,714 |
| 39 | 8-Cl | H | 894,871,845,812,787,770 |
| 40 | 8-Cl | o-F | 895,875,858,820,814,782 |
| 41 | 8-Cl | m-F | 892,884,867,860,815,771 |
| 42 | 8-Cl | p-F | 898,890,870,855,832,820 |
| 43 | 8-Cl | o-Cl | 896,885,880,848,823,789 |
| 44 | 8-Cl | p-Cl | 890,842,820,806,782,768 |
| 45 | 8-Cl | m-Cl | 890,865,815,790,777,740 |
| 46 | 8-Cl | p-NO$_2$ | 895,882,849,834,808,784 |
| 47 | 8-F | p-NO$_2$ | 896,884,869,860,828,821 |
| 48 | 8-OCH$_3$ | p-NO$_2$ | 338–340 |
| 49 | 6-Cl | p-Cl | 825,806,762,736,720 |
| 50 | 7-CF$_3$ | H | 324–327 |
| 51 | 7-CF$_3$ | p-F | 331–334 |
| 52 | 7-CF$_3$ | m-Cl | 317–320 |
| 53 | 7-CF$_3$ | p-Cl | 890,854,826,800,770,756 |

EXAMPLE 25

Preparation of 10,000 tablets each containing 5 mg of the active ingredient:

| Formula: | |
|---|---|
| 2-(p-chlorophenyl)-pyrazolo[4,3-c]-quinolin-3(5H)-one | 50.00 g |
| Lactose | 1,157.00 g |
| Corn Starch | 75.00 g |
| Polyethylene glycol 6,000 | 75.00 g |
| Talcum powder | 75.00 g |
| Magnesium stearate | 18.00 g |
| Purified water | q.s. |

PROCEDURE

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 26

Preparation of 10,000 capsules each containing 10 mg of the active ingredient:

| Formula: | |
|---|---|
| 2-phenyl-pyrazolo[4,3-c]-quinolin-3(5H)-one | 100.0 g |
| Lactose | 1,800.0 g |
| Talcum powder | 100.0 g |

PROCEDURE

All the powders are passed through a screen with openings of 0.6 mm. Then the drug substance is placed in a suitable mixer and mixed first with the talcum, then with the lactose until homogenous. No. 3 capsules are filled with 200 mg each, using a capsule filling machine.

Analogously tablets or capsules are prepared from the remaning compounds of the invention, e.g. those illustrated by the previous examples.

I claim:

1. A 2-aryl-pyrazolo[4,3-c]quinolin-3-one compound of the formulae

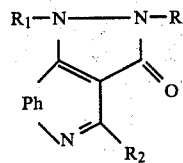

and

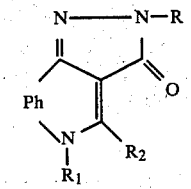

wherein Ph is 1,2-phenylene, unsubstituted or substituted by up to 3 identical or different members selected from lower alkyl, lower alkoxy, lower alkylthio, hydroxy, halogeno, trifluoromethyl, nitro, amino, mono- or di-lower alkylamino, cyano, carbamoyl and carboxy; R is unsubstituted or substituted phenyl as defined by H—Ph, pyridyl, lower alkylpyridyl or halogenopyridyl; R$_1$ is hydrogen, lower alkyl or lower (hydroxy, dialkylamino or H—Ph)-alkyl; and R$_2$ is hydrogen or lower alkyl; their 3-hydroxy-tautomers; lower alkanoyl, carbamoyl, mono- or di-lower alkylcarbamoyl derivatives of said (hydroxy or amino)-(phenyl or phenylene) compounds; or pharmaceutically acceptable alkali metal or acid addition salts thereof.

2. A compound as claimed in claim 1, in which formulae Ph is 1,2-phenylene, unsubstituted or substituted by one or two members selected from lower alkyl, lower alkoxy, lower alkylthio, hydroxy, halogeno, trifluoromethyl, nitro, amino, mono- or di-lower alkylamino, cyano, carbamoyl and carboxy; R is phenyl as defined by H—Ph, pyridyl, lower alkylpyridyl or halogenopyridyl; R$_1$ is hydrogen, lower alkyl or lower (hydroxy, dialkylamino or HPh)-alkyl, wherein the hydroxy or amino group is separated from the ring-nitrogen atom by at least 2 carbon atoms; and $R_2$ is hydrogen or lower alkyl; or lower alkanoyl, carbamoyl, mono- or di-lower alkylcarbamoyl derivatives of said (hydroxy or amino)-(phenyl or phenylene) compounds; or pharmaceutically acceptable alkali metal or acid addition salts thereof.

3. A compound as claimed in claim 1, in which formulae Ph is 1,2-phenylene, (lower alkyl)-1,2-phenylene, (lower alkoxy)-1,2-phenylene, (lower alkylthio)-1,2-phenylene, (hydroxy)-1,2-phenylene, (halogeno)-1,2-phenylene, (trifluoromethyl)-1,2-phenylene, (nitro)-1,2-phenylene, (amino)-1,2-phenylene or (mono- or di-lower alkylamino)-1,2-phenylene, (cyano)-1,2-phenylene, (carbamoyl)-1,2-phenylene or (carboxy)-1,2-phenylene; R is phenyl as defined by H—Ph, pyridyl, (lower alkyl)-pyridyl or (halogeno)-pyridyl; and each of $R_1$ and $R_2$ is hydrogen or lower alkyl; or lower alkanoyl, carbamoyl, mono- di-lower alkylcarbamoyl derivatives of said (hydroxy or amino)-(phenyl or phenylene) compounds; or pharmaceutically acceptable alkali metal or acid addition salts thereof.

4. A compound as claimed in claim 1, and corresponding to the formula

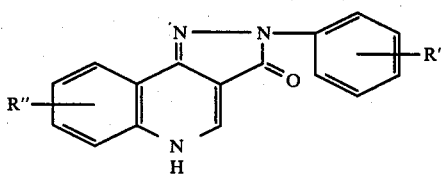

wherein R" is hydrogen, alkyl or alkoxy with up to 4 carbon atoms each, hydroxy, fluoro, chloro, bromo or trifluoromethyl; and R' is hydrogen, o- or m-fluoro; or it is p-fluoro when R" is chloro; or pharmaceutically acceptable alkali metal or acid addition salts thereof.

5. A compound as claimed in claim 1, and corresponding to the formula

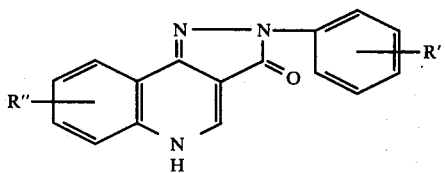

wherein R" is hydrogen, alkyl or alkoxy with up to 4 carbon atoms each, hydroxy, fluoro, chloro, bromo or trifluoromethyl; and R' is alkyl or alkoxy with up to 4 carbon atoms each, hydroxy, chloro, bromo, trifluoromethyl, nitro, amino, monoalkylamino or alkylcarbamoylamino with up to 4 carbon atoms each, or cyano; or it is p-fluoro when R" is different from chloro; or pharmaceutically acceptable alkali metal or acid addition salts thereof.

6. A compound as claimed in claim 4, wherein R" is hydrogen, or 8-(methyl, methoxy, fluoro or chloro), and R' is hydrogen; or it is 4-fluoro when R" is 8-chloro; or pharmaceutically acceptable alkali metal or acid addition salts thereof.

7. A compound as claimed in claim 5, wherein R" is hydrogen or 8-(methyl, methoxy, fluoro or chloro) and R' is methyl, methoxy, chloro, bromo, amino or cyano; or it is 4-fluoro when R" is different from 8-chloro; or pharmaceutically acceptable alkali metal or acid addition salts thereof.

8. A compound as claimed in claim 4, wherein R' is hydrogen and R" is hydrogen or 8-(methoxy, fluoro or chloro); or pharmaceutically acceptable alkali metal or acid addition salts thereof.

9. A compound as claimed in claim 5, wherein R' is 4-fluoro and R" is 8-chloro; or pharmaceutically acceptable alkali metal or acid addition salts thereof.

10. A compound as claimed in claim 4, wherein R" is hydrogen and R' is 4-(methyl, chloro or amino); or pharmaceutically acceptable alkali metal or acid addition salts thereof.

11. A compound as claimed in claim 5, and being 2-(p-chlorophenyl)-pyrazolo[4,3-c]quinolin-3(5H)-one; or the sodium salt, hydrochloride or mesylate thereof.

12. A compound as claimed in claim 4, and being 2-phenyl-pyrazolo[4,3-c]quinolin-3(5H)-one; or the sodium salt, hydrochloride or mesylate thereof.

13. An anxiolytic pharmaceutical composition, comprising an anxiolytic amount of a compound as claimed in claim 1, together with a pharmaceutical excipient.

14. A method of treating anxiety in mammals, which comprises the enteral or parenteral administration of an anxiolytic amount of a composition claimed in claim 13 to said mammals in need thereof.

15. An antidepressant pharmaceutical composition, comprising an antidepressive amount of a compound as claimed in claim 1, together with a pharmaceutical excipient.

16. A method of treating depression in mammals, which comprises the enteral or parenteral administration of an antidepressive amount of a composition claimed in claim 15 to said mammals in need thereof.

* * * * *

UNITED STATES PATENT AND TRADEMARK OFFICE
CERTIFICATE OF CORRECTION

PATENT NO. : 4,312,870
DATED : Jan. 26, 1982
INVENTOR(S) : Naokata Yokoyama

It is certified that error appears in the above—identified patent and that said Letters Patent is hereby corrected as shown below:

Claim 9, Column 20, Line 24 reads:

"A compound as claimed in claim 5, wherein R' is"

Should read:

-- A compound as claimed in claim 4, wherein R' is --

Claim 10, Column 20, Line 27 reads:

"A compound as claimed in claim 4, wherein R" is"

Should read:

-- A compound as claimed in claim 5, wherein R' is --

Signed and Sealed this

Fifteenth Day of June 1982

[SEAL]

Attest:

GERALD J. MOSSINGHOFF

Attesting Officer

Commissioner of Patents and Trademarks

UNITED STATES PATENT AND TRADEMARK OFFICE
CERTIFICATE OF CORRECTION

PATENT NO. : 4,312,870
DATED : January 26, 1982
INVENTOR(S) : Naokata Yokoyama

It is certified that error appears in the above-identified patent and that said Letters Patent is hereby corrected as shown below:

Claim 9, column 20, line 24 reads:

"A compound as claimed in claim 5, wherein R' is"

Should read:

-- A compound as claimed in claim 4, wherein R' is --

Claim 10, column 20, line 27 reads:

"A compound as claimed in claim 4, wherein R" is"

Should read:

-- A compound as claimed in claim 5, wherein R" is --

This certificate supersedes certificate of correction issued June 15, 1982.

Signed and Sealed this

Thirtieth Day of August 1983

[SEAL]

Attest:

GERALD J. MOSSINGHOFF

Attesting Officer

Commissioner of Patents and Trademarks